United States Patent [19]

Nelson

[11] 4,297,285

[45] * Oct. 27, 1981

[54] 2,3-DIHYDRO-2,3-DIMETHYL-7-BENZOFURYL N-[(PHOSPHINYL)AMINO]THIO- AND N-[(PHOSPHINOTHIOYL)AMINO]THIO-METHYLCARBAMATES

[75] Inventor: Stephen J. Nelson, Kalamazoo, Mich.

[73] Assignee: The Upjohn Company, Kalamazoo, Mich.

[*] Notice: The portion of the term of this patent subsequent to Jun. 17, 1997, has been disclaimed.

[21] Appl. No.: 174,049

[22] Filed: Jul. 31, 1980

Related U.S. Application Data

[63] Continuation-in-part of Ser. No. 115,474, Jan. 25, 1980, which is a continuation-in-part of Ser. No. 962,266, Nov. 20, 1978, Pat. No. 4,208,409, which is a continuation-in-part of Ser. No. 874,959, Feb. 3, 1978, abandoned, which is a continuation-in-part of Ser. No. 765,807, Feb. 4, 1977, Pat. No. 4,081,536.

[51] Int. Cl.$^3$ ............................................ C07D 307/86
[52] U.S. Cl. ................................................. 260/346.73
[58] Field of Search .................................... 260/346.73

[56] References Cited

U.S. PATENT DOCUMENTS 4,208,409 6/1980 Nelson ................................ 424/209

*Primary Examiner*—Henry R. Jiles
*Assistant Examiner*—Bernard Dentz
*Attorney, Agent, or Firm*—Sidney B. Williams, Jr.

[57] ABSTRACT

New phosphinic acid derivatives of aminothio methylcarbamates. The new compounds are active against insects, mites and nematodes.

34 Claims, No Drawings

2,3-DIHYDRO-2,3-DIMETHYL-7-BENZOFURYL N-[(PHOSPHINYL)AMINO]THIO- AND N-[(PHOSPHINOTHIOYL)AMINO]THIO-METHYLCARBAMATES

CROSS-REFERENCES TO RELATED APPLICATIONS

This application is a continuation-in-part of application Ser. No. 115,474, filed Jan. 25, 1980, which is a continuation-in-part of application Ser. No. 962,266, filed Nov. 20, 1978, and now U.S. Pat. No. 4,208,409, which is a continuation-in-part of application Ser. No. 874,959, filed Feb. 3, 1978, now abandoned, which is a continuation-in-part of application Ser. No. 765,807, filed Feb. 4, 1977 and now U.S. Pat. No. 4,081,536.

The present invention relates to N-[(phosphinyl)amino]-thio- and N-[(phosphinothioyl)amino]thio- methylcarbamate pesticides, having the formula

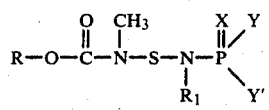

I wherein R is selected from the group consisting of

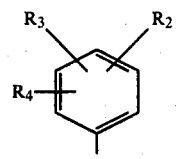

wherein $R_2$, $R_3$ and $R_4$ are of the same or different and are selected from the group consisting of hydrogen, lower-alkyl of one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and $N=CHN(CH_3)_2$;

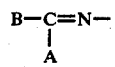

b.

wherein A and B are the same or different and are selected from the group consisting of lower-alkyl of one to five carbon atoms, inclusive, lower-alkylthio of one to five carbon atoms, inclusive, phenylthio wherein phenyl is unsubstituted or substituted with one to three substituents, same or different, selected from the group consisting of halogen and lower-alkyl of one to four carbon atoms, inclusive, monocyano substituted alkylthio of one to five carbon atoms, inclusive, cyano, alkoxy having one to five carbon atoms, inclusive, phenyl, and hydrogen, with the proviso that when A is hydrogen, B is of the formula:

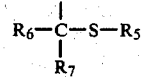

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula:

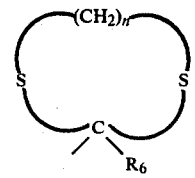

wherein n is 2 or 3 and the alkylene portion of the ring is unsubstituted or substituted with one or two methyl groups; A and B taken together with the carbon atom to which they are attached form a dithio heterocyclic of the formula:

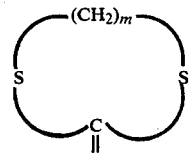

wherein m is 2 or 3 and the alkylene portion of the ring is unsubstituted or substituted with one to two methyl groups; and

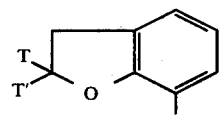

c.

wherein T and T' can be the same or different and are selected from the group consisting of hydrogen and lower alkyl of from one to six carbons; $R_1$ is selected from the group consisting of lower-alkyl, phenyl, substituted phenyl, phenyl lower-alkyl, and cycloalkyl; X is oxygen or sulfur; Y and Y' are the same or different and are selected from the group consisting of $Y_1$ and $Y'_1$ and Y and Y' taken together to form a functionality selected from the group consisting of:

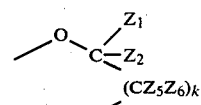

I'

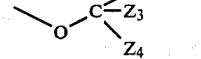

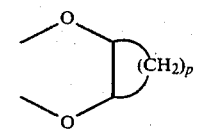

I'' and

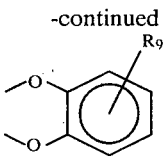

wherein $Y_1$ and $Y'_1$ are selected from the group consisting of lower-alkyl, lower alkoxy, lower-alkylthio, cycloalkyl, phenyl, substituted phenyl, phenoxy, substituted phenoxy, thiophenoxy, and substituted thiophenoxy; $Z_1$ through $Z_6$ are the same or different and are selected from the group consisting of hydrogen, methyl and ethyl; and k is 0 or 1, p is three or four and $R_9$ is selected from the group consisting of hydrogen, lower alkyl, lower alkoxy and halogen. Material constituting a disclosure of which is incorporated here by reference from U.S. Pat. No. 4,208,409.

A novel method for preparing the compounds of this invention is described in Applicant's copending application Ser. No. 132,639, filed Mar. 21, 1980. This method involves the preparation of a compound having the formula:

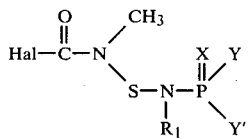

and then reacting the compound of Formula II with a compound having the formula ROH     III wherein Hal is selected from the group consisting of fluoro and chloro; and $R_1$, X, Y and Y' are as defined for Formula I above. The carbamic halides of Formula II can be prepared in accordance with one of two processes. A schematic representation of the process is shown as follows:

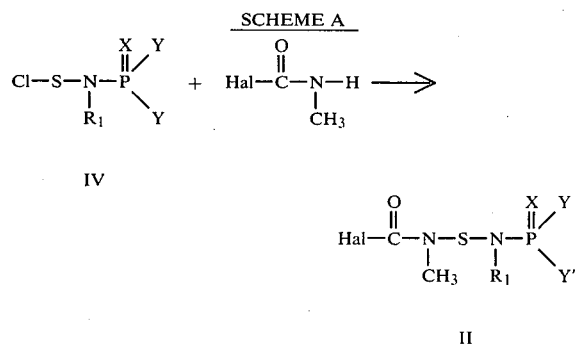

wherein $R_1$, X, Hal, Y and Y' are as defined for Formula I above.

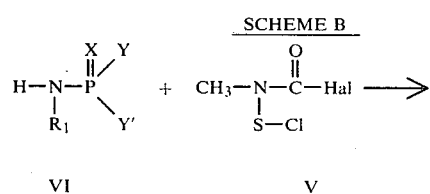

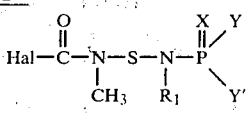

wherein $R_1$, X, Hal, Y and Y' are also as defined for Formula I above.

The N-methylcarbamoyl halide reactant used in Scheme A includes both N-methylcarbamoyl fluoride and N-methylcarbamoyl chloride. These reactants are well known in the art, however, the present invention also includes an improved method of taking N-methylcarbamoyl fluoride.

It is known that N-methylcarbamoyl fluoride can be made in the following way:

$$HF + CH_3NCO \longrightarrow CH_3NHCOF.$$

However, heretofore, solvents such as pentane or ether were employed in making it so that the product mixture could be stored and handled in conventional glassware.

It has now been discovered that N-methylcarbamoyl fluoride is readily obtained according to the above representation but in high yield and purity using conventional glassware by the addition of anhydrous hydrogen fluoride to a 0 to 50% excess and preferable 5 to 20% excess of methyl isocyanate in the absence of other solvent and at temperatures from −50° to +50° C., preferably at −20° to 20° C. In addition to the improvement in the method such that it can be carried out in the absence of a solvent, the procedure is now amenable to flow type reactors in gas or condensed phase, thereby confining the reaction to a relatively small volume which also provides the advantages of efficient cooling and confinement of hazardous materials to a small space.

N-chlorothiophosphoramide type compounds of Formula III for use in Scheme A are known in the art as disclosed in U.S. Pat. No. 4,024,277 and U.S. Pat. No. 4,081,536 or can be readily obtained by using appropriate starting materials in the procedures described therein. These appropriate starting materials are described as phosphoramide VI reactants above.

Reaction of compounds of Formula IV with N-methylcarbamoyl halide is performed in an inert solvent, preferably a polar aprotic solvent such as acetonitrile or dimethyl formamide, and in the presence of a tertiary organic base such as triethylamine as an acid acceptor. The temperature of the reaction may be −50° to +40°, preferably −30° to +10°. The resultant phosphorous amide type thiocarbamic halide intermediates having Formula $II_1$, II', and II''' are isolated by conventional means and are suitable as the intermediates as obtained in a crude state for reaction with hydroxy compounds in Step 2 above.

The alternative procedure, Scheme B, to obtain the desired intermediate II reacts as N-chlorothiomethylcarbamoyl halide IV with an appropriate phosphoramide V. The reaction is conducted in a suitably inert solvent such as dimethyl formamide, acetonitrile, ether, tetrahydrofuran, toluene, or methylene chloride in the presence of an organic base such as triethylamine, at temperatures from −20° to 50° C., preferably at −20° to 10° C. The intermediates prepared by this means are also isolated by conventional means and are suitable as obtained, i.e. without purification, for reaction with hydroxy compounds in Step 2.

Although it is indicated above that the novel intermediates are isolated in each scheme, it is not necessary to separate the intermediates from the reaction mixture of their preparation before further reaction with hydroxy compounds according to the process of this invention in obtaining the desired product, Formula I supra.

In Step 2, the reaction of hydroxy compounds III with phosphorus derivatives of aminothiocarbamic halide intermediates having Formula II is conducted in an inert solvent, preferably an aprotic polar solvent such as acetonitrile, diethylether, tetrahydrofuran and dimethyl formamide and in the presence of an organic base, such as trialkyl amine (e.g., triethylamine), pyridine and lutidine, at temperatures from 0° to 100°, preferable 10° to 50°. Alternatively the reaction may be conducted in a two phase system consisting of an inert organic solvent such as toluene or methylene chloride and an aqueous phase in which the hydroxy compound, an alkali metal hydroxide and a phase transfer reagent are dissolved. Suitable phase transfer reagents include tetraalkylammonium halides, crown ethers and benzyltrimethylammonium chloride. The reaction is conducted at 0° to 100°, preferably 20° to 50°. The product of the invention process is isolated by conventional means such as by filtration, solvent evaporations, crystallization or chromatography.

The following Examples are indicative of the scope of this invention and are not to be construed as limitative. Those skilled in the art will promptly recognize appropriate variations from the procedure both as to methylcarbamate percursors as well as reaction conditions and techniques. These examples indicate the best mode presently known to the inventor.

EXAMPLE 1

Methyl N-[[[[[(1,1-dimethylethyl)(5,5-dimethyl-2-oxo-1,3,2-dioxaphosphorinan-2-yl)amino]thio]methylamino]carbonyl]oxy]ethanimidothiate

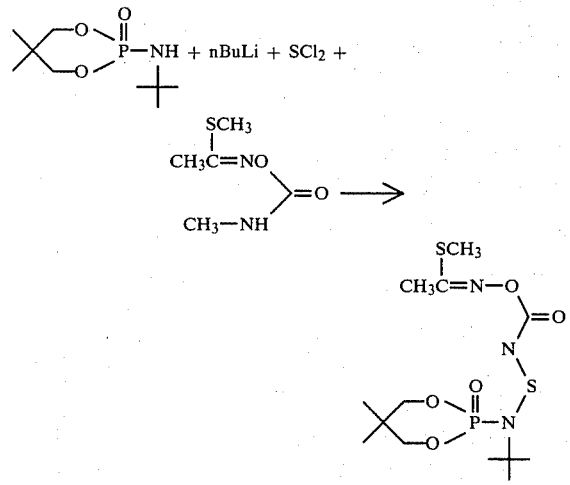

To a slurry of N-(5,5-dimethyl-2-oxo-1,3,2-dioxaphosphorinan-2-yl)-1,1-dimethylethanamine (15.7 g., 70.8 mmoles) in tetrahydrofuran (50 ml.) at −5° is added over a ten minute period a solution of n-butyl lithium in hexane (46 ml. of 1.6 M; 74 mmoles) with rapid stirring under dry nitrogen. This is stirred for 60 minutes at −5° and then transferred under dry nitrogen to an addition funnel and added over a 30 minute period to a solution of freshly distilled sulfur dichloride in tetrahydrofuran (25 ml.) at −5° with stirring. Stirring is continued for two hours at −5° and then filtered under dry nitrogen. The filter cake is washed with tetrahydrofuran (50 ml.) and the filtrates combined and concentrated in vacuo at ≦35°. The residue is redissolved in tetrahydrofuran (75 ml.), cooled to −5°, solid cuprous chloride 0.3 g.) added at once followed immediately by the addition of a solution of methomyl (11.5g.; 70.8 mmoles) and triethylamine (9.8 ml., 70.8 mmoles) with stirring under dry nitrogen. About four monutes are required. Stirring is continued for two hours at −5°. The reaction mixture is then concentrated in vacuo at ≦45°, and the residue taken up in methylene chloride (500 ml.) and washed with ice-water (2×300 ml.). The organic phase is vacuum filtered through celite and dried (anhydrous sodium sulfate). It is then concentrated in vacuo at ≦45° giving 28 g. of viscous oil. Preliminary absorption chromatography on silica gel using 2:1 ethyl acetate:Skellysolve B gives 15 g. of yellow oil. Chromatography of this material on silica gel using 1:4 isopropanol:Skellysolve B gives 4.4 g. (15% yld) as a white crystalline solid; MP 133.5°–134.5° (recrystallized from ethylacetate).

Analysis: Calc'd. for $C_{14}H_{28}N_3O_5PS_2$: C, 40.67; H, 6.83; N, 10.16; Found: C, 40.48; H, 7.04; N, 9.95.

EXAMPLE 2

Methyl N-[[[methyl[[(1-methylethyl) (2-oxo-1,3,2-dioxaphos-phorinan-2-yl)amino]thio]amino]carbonyl-]oxy]ethanimidothioate

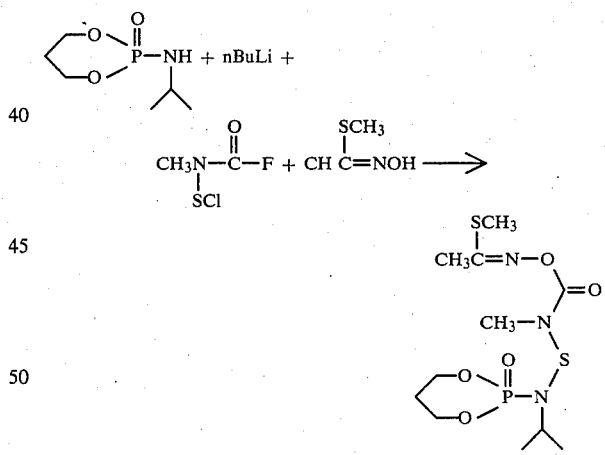

To a solution of N-(1-methylethyl)-2-oxo-1,3,2-dioxaphosphorinan-2-amine (12.7 g.; 70.8 mmoles) in tetrahydrofuran (50 ml.) is added n-butyl lithium in n-hexane (46 ml. of 1.6 M; 74 moles) with stirring under dry nitrogen at 0° over a ten minute period. Stirring is continued at 0° to 25° for two hours. The reaction mixture is transferred under dry nitrogen to an addition funnel and added dropwise to a solution of N-chlorothio-N-methylcarbamic fluoride (10.2 g.; 70.8 mmoles) in tetrahydrofuran (50 ml.) with stirring under dry nitrogen at −5°. Approximately ten minutes are required. Stirring is continued for two hours at 0° to 25°. The reaction mixture is cooled to 0° and solid methyl N-hydroxy ethanimidothioate (7.45 g.; 70.8 mmoles) added at once under nitrogen with rapid stirring. This is followed immediately by the dropwise addition of triethylamine (9.8 ml.; 70.8 mmoles) over a period of ten minutes. The reaction mixture is stirred at 0° to 25° under dry nitrogen overnight. It is then gravity filtered and the filtrate concentrated in vacuo giving 25 g. of dark brown oil. This is subjected to absorption chromatography on silica gel; this is eluted stepwise with 70% ethylacetate in Skellysolve B, 100% ethylacetate, and finally 100% acetone giving 10/8 g. of brown crystalline solid. Silica gel chromatography on this material in which 50% acetone in Skellysolve B is the eluant gives 1/98 g. (7.5% yield) of a white crystalline solid; M.P. 134°–135° after recrystallization from ethylacetate.

Analysis: Calc'd. for $C_{11}H_{22}N_3O_5PS_2$: C, 35.57; H, 5.97; N, 11.31; Found: C, 35.61; H, 5.83; N,11.30.

EXAMPLE 3

Utilizing the procedure of Examples 1 and 2 but substituting the appropriate phosphinic acid amide for N-(5,5-dimethyl-2-oxo-1,3,2-dioxaphosphorinan-2-yl)-1,1-dimethylethanamine and N-(1-methylethyl)-2-oxo-1,3,2-dioxaphosphorinan-2-amine respectively, the following compounds are prepared.

2-methyl-2-(methylthio)-0-[[[[(5,5-dimethyl-2-thioxo-1,3,2-dioxaphosphorinan-2-yl)(1-methylethyl)amino]-thio]methylamino]carbonyl]propanal oxime, m.p. 114° C.(d).

Analysis: Calc'd. for $C_{15}H_{30}H_3OS_3$: C, 40.62; H, 6.82; N, 9.47; S, 21.68; Found: C, 40.14; H, 7.42; N, 9.40; S, 23.50.

O-[[[[(5,5-dimethyl-2-thioxo-1,3,2-dioxaphosphorinan-2-yl)(1-methylethyl)amino]thio]methylamino]carbonyl]-1,3-dithiolan-2-one oxime, m.p. 134°–135.5°.

Analysis: Calc'd. for $C_{13}H_{24}N_3O_4PS_4$: C, 35.04; H, 5.43; N, 9.43; S, 28.78; Found: C, 35.14; H, 5.53; N, 9.46; 5, 30.04.

N-cyclohexyl-N-[[[[(1,3-dithiolan-2-ylidenamino)oxy]carbonyl]methylamino]thio]-5,5-dimethyl-1,3,2-dioxaphosphorinan-2-amino-2-sulfide, m.p. 146°–147.5°.

Analysis: Calc'd. for $C_{16}H_{28}N_3O_4PS_4$: C, 39.57; H, 5.81; N, 8.65; S, 26.41; Found: C, 39.88; H, 6.17; N, 8.72; S, 28.90.

Syn and anti-O-[[[[cyclohexyl(5,5-dimethyl-2-thioxo-1,3,2-dioxaphosphorinan-2-yl)amino]thio]methylamino]carbonyl]-2-methyl-2-(methylthio)propanal oxime, m.p. 108°–115° C.

Analysis: Calc'd. for $C_{18}H_{34}N_3O_4PS_3$: C, 44.70; H, 7.09; N, 8.69; Found: C, 44.61; H, 7.38; N, 9.04.

Methyl N-[[[[[cyclohexyl(5,5-dimethyl-2-oxo-1,3,2-phosphorinan-2-yl)amino]thio]methylamino]carbonyl-]oxy]ethanimidothioate, m.p. 145°.

Analysis: Calc'd. for $C_{16}H_{30}N_3O_5PS_2$: C, 43.72; H, 6.88; N, 9.56; Found: C, 43.35; H, 6.87; N, 9.00.

3(1,1-dimethylethyl)phenyl methyl [[(1-methylethyl)(2-thioxo-1,-3,2-dioxaphosphorinan-2-yl)amino]-thio]-carbamate, as an oil.

Analysis: Calc'd. for $C_{18}H_{29}N_24PS_2$: C, 49.98; H, 6.76, N, 6.48; Found: C, 50.27; H, 6.93; N, 6.25.

2-chloro-3,4-dimethylphenyl methyl[[cyclohexyl(5,5-dimethyl-2-thioxo-1,3,2-dioxaphosphorinan-2-yl)amino]thio]carbamate, m.p. 147°–148° C. Analysis: Calc'd. for $C_{21}H_{32}ClN_2O_4PS_2$: C, 49.74; H, 6.36; N, 5.52; Found: C, 50.03; H, 6.54; N, 5.46.

Methyl N-[[[[[(3,4-dimethylphenyl)(5,5-dimethyl-2-oxo-1,3,2-dioxaphosphorinan-2-yl)amino]thio]methylamino]carbonyl]oxy-ethanimidothioate, m.p. 120°–122° C.

Analysis: Calc'd. for $C_{18}H_{28}N_3O_5PS_2$: C, 46.84; H, 6.12; N, 9.10; Found: C, 46.52; H, 6.40; N, 8.91.

Methyl N-[[[methyl[[(benzyl)(2-thioxo-1,3,2-dioxaphosphorinan-2-yl)amino]thio]amino]carbonyl]oxy]ethanimidothioate, as an oil.

Analysis: Calc'd. for $C_{15}H_{22}N_3O_4PS_3$: C, 41.37; H, 5.09; N, 9.65; Found: C, 41.45; H, 4.89; N, 9.61.

EXAMPLE 4

2,3-dihydro-2,2-dimethyl-7-benzofuranyl methyl[[(1-methylethyl)(2-thioxo-1,3,2-dioxaphosphorinan-2-yl)amino]thio]carbamate (a) A solution of triethylamine (7.17 g., 70.8 mmol) in diethylether is added over ten minutes to a solution of N-methylcarbamoyl fluoride (5.46 g., 70.8 mmol) and sulfur dichloride (8.10 g., 78.7 mmol) in diethylether maintaining a reaction temperature of −5° to 0°. After the addition the mixture is stirred at 0° for 90 minutes and the precipitated salts filtered and washed with diethylether. The combined filtrates are concentrated in vacuo to leave N-chlorothio(methyl)carbamoyl fluoride as a yellow oil.

(b) The yellow oil obtained in (a) is dissolved in tetrahydrofuran (50 ml.) and added dropwise over 10 minutes to a solution of 2-(1-methylethamino)-2-thioxo-1,3,2-dioxaphosphorinane (13.8 g., 70.8 mmol) in tetrahydrofuran maintaining a reaction temperature of −5° to 0°. After the addition the mixture is stirred at 0° for 90 minutes then diluted with diethylether (200 ml.) and washed with ice water, brine, and dried over sodium sulfate. The solvents are removed and the residue is dissolved in 50 ml. of methylene chloride.

(c) A solution of 2,3-dihydro-2,2-dimethyl-7-benzofuranyl, sodium hydroxide (2.83 g., 70.8 mmol) and tetraethylammonium chloride (1.0 g.) in water (50 ml.) is added to the solution of methylene chloride and N-methyl [[(1-methylethyl)(2-thioxo-1,3,2-dioxaphosphorinan-2-yl)amino]thio]carbamoyl fluoride obtained in (b) and the mixture vigorously stirred for 18 hours. The phases are separated, the organic phase washed with water, dried over sodium sulfate and concentrated under reduced pressure. Chromatography of the residue over silica gel eluting with 15% acetone in hexane gives the title compound as a colorless viscous oil. The ir and pmr spectra are consistent with the desired structure.

Analysis Calc'd. for $C_{18}H_{27}N_2O_5PS_2$ (446.53): C, 48.42; H, 6.10; N, 6.27; Found: C, 48.48; H, 6.86; N, 6.16. Mass spectrum M/e 446.

Utilizing the procedure of Example 4, but substituting the appropriate carbamoyl fluoride prepared in a manner similar to step (b), for N-methyl[[(1-methylethyl)(2-thioxo-1,3,2-dioxaphosphorinan-2-yl)amino]thio]carbamoyl fluoride there is obtained:

2,3-dihydro-2,2-dimethyl-7-benzofuranyl methyl[[(methyl)(5,5-dimethyl-2-thioxo-1,3,2-dioxaphosphorinan-2-yl)-amino]thio]carbamate 2,3-dihydro-2,2-dimethyl-7-benzofuranyl methyl[[(ethyl) (5,5-dimethyl-2-thioxo-1,3,2-dioxaphosphorian-2-yl)amino]thio]carbamate 2,3-dihydro-2,2-dimethyl-7-benzofuranyl methyl[[(ethyl)(5,5-dimethyl-2-thioxo-1,3,2-dioxaphosphorinan-2-yl)amino]thio]carbamate 2,3-dihydro-2,2-dimethyl-7-benzofuranyl methyl[[(1-methylethyl)-(5,5-dimethyl-2-thioxo-1,3,2-dioxaphosphorinan-2-yl)amino]thio-carbamate 2,3-dihydro-2,2-dimethyl-7-benzofuranyl methyl[[(n-butyl-(5,5-dimethyl-2-thioxo-1,3,2-dioxaphosphorinan-2-yl)amino]thio]carbamate 2,3-dihydro-2,2-dimethyl-7-benzofuranyl methyl[[(1,1-dimethylethyl) (5,5-dimethyl-2-thioxo-1,3,2-dioxaphosphorinan-2-yl)amino]thio]carbamate 2,3-dihydro-2,2-dimethyl-7-benzofuranyl methyl[[(cyclohexyl-(5,5-dimethyl-2-thioxo-1,3,2-dioxaphosphorinan-2-yl)amino]thio]carbamate 2,3-dihydro-2,2-dimethyl-7-benzofuranyl methyl[[(benzyl)(5,5-dimethyl-2-thioxo-1,3,2-dioxaphosphorinan-2-yl)amino]thio]carbamate 2,3-dihydro-2,2-dimethyl-7-benzofuranyl methyl[[(-phenyl)(5,5-dimethyl-2-thioxo-1,3,2-dioxaphosphorinan-2-yl)amino]thio]carbamate 2,3-dihydro-2,2-dimethyl-7-benzofuranyl methyl[[(1,1-dimethylpropyl) (5,5-dimethyl-2-thioxo-1,3,2-dioxaphosphorinan-2-yl)amino]thio]carbamate 2,3-dihydro-2,2-dimethyl-7-benzofuranyl methyl[[(methyl)(5,5-dimethyl-2-oxo-1,3,2-dioxaphosphorinan-2-yl)amino]thio]carbamate 2,3-dihydro-2,3-dihydro-2,2-dimethyl-7-benzofuranyl methyl[[(ethyl) (5,5-dimethyl-2-oxo-1,3,2-dioxaphosphorinan-2-yl)amino]tthio]carbamate 2,3-dihydro-2,2-dimethyl-7-benzofuranyl methyl[[(1-methylethyl)(5,5-dimethyl-2-oxo-1,3,2-dioxaphosphorinan-2-yl)amino]thio]carbamate 2,3-dihydro-2,2-dimethyl-7-benzofuranyl methyl[[(n-butyl)(5,5-dimethyl-2-oxo-1,3,2-dioxaphosphorinan-2-yl)amino]thio]carbamate 2,3-dihydro-2,2-dimethyl-7-benzofuranyl methyl[[(1,1-dimethylethyl)(5,5-dimethyl-2-oxo-1,3,2-dioxaphosphorinan-2-yl)amino]thio]carbamate 2,3-dihydro-2,2-dimethyl-7-benzofuranyl methyl[[(methyl)(2-thioxo-1,3,2-dioxaphospholan-2-yl)amino]thio]carbamate 2,3-dihydro-2,2-dimethyl-7-benzofuranyl methyl[[(1-methylethyl)(2-thioxo-1,3,2-dioxaphospholan-2-yl)amino]thio]carbamate 2,3-dihydro-2,2-dimethyl-7-benzofuranyl methyl[[(1,1-dimethylethyl)(2-thioxo-1,3,2-dioxaphospholan-2-yl)amino]thio]carbamate 2,3-dihydro-2,2-dimethyl-7-benzofuranyl methyl[[(n-butyl)(4-methyl-2-oxo-1,3,2-dioxaphospholan-2-yl)amino]thio]carbamate 2,3-dihydro-2,2-dimethyl-7-benzofuranyl methyl[[(phenyl) (4-methyl-2-oxo-1,3,2-dioxaphospholan-2-yl)amino]thio]carbamate 2,3-dihydro-2,2-dimethyl-7-benzofuranyl methyl[[(1,1-dimethylpropyl)(4-methyl-2-oxo-1,3,2-dioxaphospholan-2-yl)amino]thio]carbamate 2,3-dihydro-2,2-dimethyl-7-benzofuranyl methyl[[(1-methylethyl)(2-thioxo-1,3,2-dioxaphosphorinan-2-yl)amino]thio]carbamate 2,3-dihydro-2,2-dimethyl-7-benzofuranyl methyl[[(1,1-dimethylethyl)(2-thioxo-1,3,2-dioxaphosphorinan-2-yl)amino]thio]carbamate 2,3-dihydro-2,2-dimethyl-7-benzofuranyl methyl[[(3,4-dimethylphenyl)(2-thioxo-1,3,2-diosaphosphorinan-2-yl)amino]thio]carbamate 2,3-dihydro-2,2-dimethyl-7-benzofuranyl methyl[[(n-butyl)(2-oxo-1,3,2-dioxaphosphorinan-2-yl)amino]thio]carbamate 2,3-dihyro-2,2-dimethyl-7-benzofuranyl methyl[[(1-methylethyl)(2-oxo-1,3,2-dioxaphosphorinan-2-yl)amino]thio]carbamate 2,3-dihydro-2,2-dimethyl-7-benzofuranyl methyl[[(2-methylpropyl)(2-oxo-1,3,2-dioxaphosphorinan-2-yl)amino]thio]carbamate 2,3-dihydro-2,2-dimethyl-7-benzofuranyl methyl[[(methyl)(5,5-diethyl-2-thioxo-1,3,2-dioxaphosphorinan-2-yl)amino]thio]carbamate 2,3-dihydro-2,2-dimethyl-7-benzofuranyl methyl[[(methylethyl)(5,5-diethyl-2-thioxo-1,3,2-dioxaphosphorinan-2-yl)amino]thio]carbamate 2,3-dihydro-2,2-dimethyl-7-benzofuranyl methyl[[(4-chlorophenyl)(5,5-diethyl-2-thioxo-1,3,2-dioxaphosphorinan-2-yl)amino]thio]carbamate 2,3-dihydro-2,2-dimethyl-7-benzofuranyl methyl[[(ethyl)(4,4,6-trimethyl-2-thioxo-1,3,2-dioxaphosphorinan-2-yl)amino]thio]carbamate 2,3-dihydro-2,2-dimethyl-7-benzofuranyl methyl[[(1-methylethyl)(4,4,6-trimethyl-2-thioxo-1,3,2-dioxaphosphorinan-2-yl)amino]thio]carbamate 2,3-dihydro-2,2-dimethyl-7-benzofuranyl methyl[[(2,2-dimethylpropyl)(4,4,6-trimethyl-2-thioxo-1,3,2-dioxaphosphorinan-2-yl)amino]thio]carbamate 2,3-dihydro-2,2-dimethyl-7-benzofuranyl methyl[[(1-methylethyl (5,5-diethyl-2-oxo-1,3,2-dioxaphosphorinan-2-yl)amino]thio]carbamate 2,3-dihydro-2,2-dimethyl-7-benzofuranyl methyl[[(1,1-dimethylethyl)(5,5-diethyl-2-oxo-1,3,2-dioxaphosphorinan-2-yl)amino]thio]carbamate.

I claim:

1. 2,3-dihydro-2,2-dimethyl-7-benzofuranyl methyl[[-(methyl)(5,5-dimethyl-2-thioxo-1,3,2-dioxaphosphorinan-2-yl)-amino]thio]carbamate.

2. 2,3-dihydro-2,2-dimethyl-7-benzofuranyl methyl[-[(ethyl) (5,5-dimethyl-2-thioxo-1,3,2-dioxaphosphorinan-2-yl)amino]thio]carbamate.

3. 2,3-dihydro-2,2-dimethyl-7-benzofuranyl methyl[[(1-methylethyl)(5,5-dimethyl-2-thioxo-1,3,2-dioxaphosphorinan-2-yl)amino]thio]carbamate.

4. 2,3-dihydro-2,2-dimethyl-7-benzofuranyl methyl[[(n-butyl-(5,5-dimethyl-2-thioxo-1,3,2-dioxaphosphorinan-2-yl)amino]thio]carbamate.

5. 2,3-dihydro-2,2dimethyl-7-benzofuranyl methyl[[(1,1-dimethylethyl) (5,5-dimethyl-2-thioxo-1,3,2-dioxaphosphorinan-2-yl)amino]thio]carbamate.

6. 2,3-dihydro-2,2-dimethyl-7-benzofuranyl methyl[[-(cyclohexyl-(5,5-dimethyl-2-thioxo-1,3,2-dioxaphosphorinan-2-yl)amino]thio]carbamate.

7. 2,3-dihydro-2,2-dimethyl-7-benzofuranyl methyl[[-(benzyl)(5,5-dimethyl-2-thioxo-1,3,2-dioxaphosphorinan-2-yl)amino]thio]carbamate.

8. 2,3-dihydro-2,2-dimethyl-7-benzofuranyl methyl[[(phenyl)(5,5-dimethyl-2-thioxo-1,3,2-dioxaphosphorinan-2-yl)amino]thio]carbamate.

9. 2,3-dihydro-2,2-dimethyl-7-benzofuranyl methyl[[(1,1-dimethylpropyl)(5,5-dimethyl-2-thioxo-1,3,2-dioxaphosphorinan-2-yl)amino]thio]carbamate.

10. 2,3-dihydro-2,2-dimethyl-7-benzofuranyl methyl[[(methyl)(5,5-dimethyl-2-oxo-1,3,2-dioxaphosphorinan-2-yl)amino]thio]carbamate.

11. 2,3-dihydro-2,2-dimethyl-7-benzofuranyl methyl[-[(ethyl)(5,5-dimethyl-2-oxo-1,3,2-dioxaphosphorinan-2-yl)amino]thio[carbamate.

12. 2,3-dihydro-2,2-dimethyl-7-benzofuranyl methyl[[(1-methylethyl)(5,5-dimethyl-2-oxo-1,3,2-dioxaphosphorinan-2-yl)amino]thio]carbamate.

13. 2,3-dihydro-2,2-dimethyl-7-benzofuranyl methyl[[(n-butyl)(5,5-dimethyl-2-oxo-1,3,2-dioxaphosphorinan-2-yl)amino]thio]carbamate.

14. 2,3-dihydro-2,2-dimethyl-7-benzofuranyl methyl[[(1,1-dimethylethyl)(5,5-dimethyl-2-oxo-1,3,2-dioxaphosphorinan-2-yl)amino]thio]carbamate.

15. 2,3-dihydro-2,2-dimethyl-7-benzofuranyl methyl[[(methyl)(2-thioxo-1,3,2-dioxaphospholan-2-yl)amino]thio]carbamate.

16. 2,3-dihydro-2,2-dimethyl-7-benzofuranyl methyl[[(1-methylethyl)(2-thioxo-1,3,2-dioxaphospholan-2-yl)amino]thio]carbamate.

17. 2,3-dihydro-2,2-dimethyl-7-benzofuranyl methyl[[(1,1-dimethylethyl)(2-thioxo-1,3,2-dioxaphospholan-2-yl)amino]thio]carbamate.

18. 2,3-dihydro-2,2-diemthyl-7-benzofuranyl methyl[[(n-butyl)(4-methyl-2-oxo-1,3,2-dioxaphospholan-2-yl)amino]thio]carbamate.

19. 2,3-dihydro-2,2-dimethyl-7-benzofuranyl methyl[[(phenyl)(4-methyl-2-oxo-1,3,2-dioxaphospholan-2-yl)amino]thio]carbamate.

20. 2,3-dihydro-2,2-dimethyl-7-benzofuranyl methyl[[(1,1-dimethylpropyl)(4-methyl-2-oxo-1,3,2-dioxaphospholan-2-yl)amino]thio]carbamate.

21. 2,3-dihydro-2,2-dimethyl-7-benzofuranyl methyl[[(1-methylethyl)(2-thioxo-1,3,2-dioxaphosphorinan-2-yl)amino]thio]carbamate.

22. 2,3-dihydro-2,2-dimethyl-7-benzofuranyl methyl[[(1,1-dimethylethyl)(2-thioxo-1,3,2-dioxaphosphorinan-2-yl)amino]thio]carbamate.

23. 2,3-dihydro-2,2-dimethyl-7-benzofuranyl methyl[[(3,4-dimethylphenyl)(2-thioxo-1,3,2-dioxaphosphorinan-2-yl)amino]thio]carbamate.

24. 2,3-dihydro-2,2-dimethyl-7-benzofuranyl methyl[[(n-butyl)(2-oxo-1,3,2-dioxaphosphorinan-2-yl)amino]thio]carbamate.

25. 2,3-dihydro-2,2-dimethyl-7-benzofuranyl methyl[[(1-methylethyl)(2-oxo-1,3,2-dioxaphosphorinan-2-yl)amino]thio]carbamate.

26. 2,3-dihydro-2,2-dimethyl-7-benzofuranyl methyl[[(2-methylpropyl)(2-oxo-1,3,2-dioxaphosphorinan-2-yl)amino]thio]carbamate.

27. 2,3-dihydro-2,2-dimethyl-7-benzofuranyl methyl[[(methyl)(5,5-diethyl-2-thioxo-1,3,2-dioxaphosphorinan-2-yl)amino]thio]carbamate.

28. 2,3dihydro-2,2-dimethyl-7-benzofuranyl methyl[[(methylethyl)(5,5-diethyl-2-thioxo-1,3,2-dioxaphosphorinan-2-yl)amino-]thio-]carbamate.

29. 2,3-dihydro-2,2-dimethyl-7-benzofuranyl methyl[[(4-chlorophenyl)(5,5-diethyl-2-thioxo-1,3,2-dioxaphosphorinan-2-yl)amino]thio]carbamate.

30. 2,3-dihydro-2,2-dimethyl-7-benzofuranyl methyl[-[(ethyl)(4,4,6-trimethyl-2-thioxo-1,3,2-dioxaphosphorinan-2-yl)amino]thio]carbamate.

31. 2,3-dihydro-2,2-dimethyl-7-benzofuranyl methyl[[1-methylethyl)(4,4,6-trimethyl-2-thioxo-1,3,2-dioxaphosphorinan-2-yl)amino]thio]carbamate.

32. 2,3-dihydro-2,2-dimethyl-7-benzofuranyl methyl[[(2,2-dimethylpropyl)(4,4,6-trimethyl-2-thioxo-1,3,2-dioxaphosphorinan-2-yl)amino]thio]carbamate.

33. 2,3-dihydro-2,2-dimethyl-7-benzofuranyl methyl[[(1-methylethyl(5,5-diethyl-2-oxo-1,3,2-dioxaphosphorinan-2-yl)amino]thio]carbamate.

34. 2,3-dihydro-2,2-dimethyl-7-benzofuranyl methyl[[(1,1-dimethylethyl)(5,5-diethyl-2-oxo-1,3,2-dioxaphosphorinan-2yl)amino]thio]carbamate.

* * * * *